(12) United States Patent
Mustapha et al.

(10) Patent No.: US 8,834,500 B2
(45) Date of Patent: Sep. 16, 2014

(54) HAND-HELD VEIN REMOVAL DEVICE

(75) Inventors: Jihad Mustapha, Ada, MI (US); Jose I. Almeida, Miami, FL (US); Edward Mackay, II, Largo, FL (US); Julian J. Javier, Naples, FL (US)

(73) Assignee: Vascular Solutions, Inc., Minneapolis, MN (US)

( * ) Notice: Subject to any disclaimer, the term of this patent is extended or adjusted under 35 U.S.C. 154(b) by 410 days.

(21) Appl. No.: 13/410,440

(22) Filed: Mar. 2, 2012

(65) Prior Publication Data

US 2012/0226297 A1    Sep. 6, 2012

Related U.S. Application Data

(60) Provisional application No. 61/449,334, filed on Mar. 4, 2011.

(51) Int. Cl.
*A61B 17/3205* (2006.01)
*A61B 17/00* (2006.01)

(52) U.S. Cl.
CPC .............................. *A61B 17/00008* (2013.01)
USPC .......................................... 606/167; 606/159

(58) Field of Classification Search
CPC ...................... A61B 17/00008; A61B 17/3207; A61B 17/3209; A61B 17/32093; A61B 17/3211; A61B 2017/32113
USPC ............. 606/1, 159, 167, 170, 171, 182, 185; 600/36; 128/207.29, 897, 898
See application file for complete search history.

(56) References Cited

U.S. PATENT DOCUMENTS

| | | | | |
|---|---|---|---|---|
| 3,905,101 | A | * | 9/1975 | Shepherd .......................... 30/162 |
| 4,203,446 | A | * | 5/1980 | Hofert et al. .................. 606/182 |
| 5,397,333 | A | * | 3/1995 | Knoepfler ...................... 606/170 |
| 5,411,512 | A | * | 5/1995 | Abidin et al. .................. 606/167 |
| 5,758,665 | A | * | 6/1998 | Suval .............................. 128/898 |
| 5,792,168 | A | * | 8/1998 | Suval .............................. 606/185 |
| 5,871,496 | A | * | 2/1999 | Ginn et al. ..................... 606/190 |
| 6,110,190 | A | * | 8/2000 | Ginn et al. ..................... 606/190 |
| 6,280,455 | B1 | * | 8/2001 | Ginn et al. ..................... 606/190 |
| 6,453,906 | B1 | * | 9/2002 | Taylor et al. .................. 128/898 |
| 6,527,771 | B1 | * | 3/2003 | Weadock et al. ............... 606/50 |
| 6,808,531 | B2 | * | 10/2004 | Lafontaine et al. ........... 606/159 |
| 7,308,896 | B2 | * | 12/2007 | Cruz ......................... 128/207.29 |
| 7,455,675 | B2 | * | 11/2008 | Schur et al. ................... 606/139 |
| 7,473,262 | B2 | * | 1/2009 | Fogarty et al. ................ 606/159 |
| 7,632,289 | B2 | * | 12/2009 | Majlessi ........................ 606/159 |
| 7,651,503 | B1 | * | 1/2010 | Coe et al. ....................... 606/108 |
| 8,034,070 | B2 | | 10/2011 | Tal |

(Continued)

*Primary Examiner* — Ryan Severson
(74) *Attorney, Agent, or Firm* — Schwegman Lundberg & Woessner, P.A.

(57) ABSTRACT

A vein removal device includes a housing, a blade element disposed at least partially within the housing, and a hook element disposed at least partially within the housing. A cutting edge of the blade element is selectively exposed for making an incision in a patient. The blade element is disposed at one end of the housing and the hook element may be disposed at an opposite end of the housing. The blade element may be selectively exposed via actuation of a first user input that imparts a movement of the blade element relative to the housing and towards an extended position where the cutting edge of the blade element is exposed. The blade element may be biased toward the extended position via a biasing element, which may urge the blade element toward the extended position responsive to actuation of the first user input.

30 Claims, 5 Drawing Sheets

(56) References Cited

U.S. PATENT DOCUMENTS

| | | | |
|---|---|---|---|
| 8,608,763 B1 * | 12/2013 | Jurbala | 606/170 |
| 8,608,767 B2 * | 12/2013 | Tal | 606/185 |
| 2003/0125759 A1 * | 7/2003 | Mirizzi et al. | 606/159 |
| 2004/0087967 A1 * | 5/2004 | Schur et al. | 606/108 |
| 2004/0204719 A1 * | 10/2004 | Fogarty et al. | 606/113 |
| 2005/0216048 A1 | 9/2005 | Suval et al. | |
| 2005/0245914 A1 * | 11/2005 | Camus et al. | 606/1 |
| 2005/0279363 A1 * | 12/2005 | Cruz | 128/207.29 |
| 2007/0100359 A1 * | 5/2007 | Majleesi | 606/159 |
| 2008/0071304 A1 * | 3/2008 | Tal | 606/190 |
| 2010/0030247 A1 * | 2/2010 | Pikus et al. | 606/159 |
| 2010/0089405 A1 * | 4/2010 | Johnson et al. | 128/207.29 |
| 2011/0264124 A1 * | 10/2011 | Boyle et al. | 606/159 |
| 2011/0301624 A1 * | 12/2011 | Tal | 606/159 |
| 2012/0226297 A1 * | 9/2012 | Mustapha et al. | 606/159 |
| 2013/0066164 A1 * | 3/2013 | Nakamura | 600/247 |
| 2013/0072964 A1 * | 3/2013 | Sarradon | 606/205 |
| 2013/0253551 A1 * | 9/2013 | Boyle et al. | 606/159 |

* cited by examiner

HAND-HELD VEIN REMOVAL DEVICE

CROSS REFERENCE TO RELATED APPLICATION

The present application claims the filing benefits of U.S. provisional application Ser. No. 61/449,334, filed Mar. 4, 2011, which is hereby incorporated herein by reference in its entirety.

FIELD OF THE INVENTION

The present invention relates to devices for removal of unwanted veins, such as varicose veins or the like, from a patient and, more particularly, to a single hand held device for making an incision in a patient retracting or pulling the unwanted vein or veins from the patient.

BACKGROUND OF THE INVENTION

It is known to remove varicose veins from a patient by making an incision in the patient near a varicose vein and pulling or extracting varicose vein at the incision. Typically, a conventional scalpel is used to make the incision and then a separate J-shaped hook is used to hook the vein and extract the vein through the incision.

SUMMARY OF THE INVENTION

The present invention provides a disposable hand held varicose vein removal device or tool that provides a blade or scalpel and a hook or extractor combined as part of a unitary device. The blade and hook may be housed within a plastic housing and may be selectively exposed for use during a vein extraction procedure.

According to an aspect of the present invention, a vein removal device includes a housing, a blade element disposed at least partially within the housing, and a hook element disposed at least partially within the housing. A cutting edge of the blade element is selectively exposed for making an incision in a patient, and the hook element is selectively exposed for hooking a vein at the incision in the patient and retracting the vein.

Optionally, the blade element may be disposed at one end of the housing and the hook element may be disposed at an opposite end of the housing. Optionally, the blade element and hook element may be disposed in and selectively exposed at a common end of the housing.

Optionally, the blade element may be selectively exposed via actuation of a first user input that imparts a movement of the blade element relative to the housing and towards an extended position where the cutting edge of the blade element is exposed. The blade element may be extended to the extended position and then automatically retracted from the extended position in response to actuation of the first user input. Optionally, the blade element may be biased towards the retracted position via a biasing element, and the biasing element may urge the blade element toward the retracted position responsive to release of the first user input or a further actuation of the first user input (such as via a further movement of the first user input or a release of the first user input by the operator or user of the vein removal device or tool). Optionally, the blade element may be biased toward the extended position via a biasing element and the biasing element may urge the blade element toward the extended position responsive to actuation of the first user input (and the blade may be further biased back towards its retracted position, such as in response to a release of the first user input or a further actuation of the first user input or in response to the blade reaching a predetermined degree of extension or the like). Optionally, the hook element may be selectively exposed via actuation of a second user input that imparts a movement of the hook element relative to the housing and towards an extended position where the hook element is exposed.

These and other objects, advantages, purposes and features of the present invention will be more fully understood and appreciated by reference to the below description of the preferred embodiments and the drawings.

DESCRIPTION OF THE PREFERRED EMBODIMENTS

Figure 1:
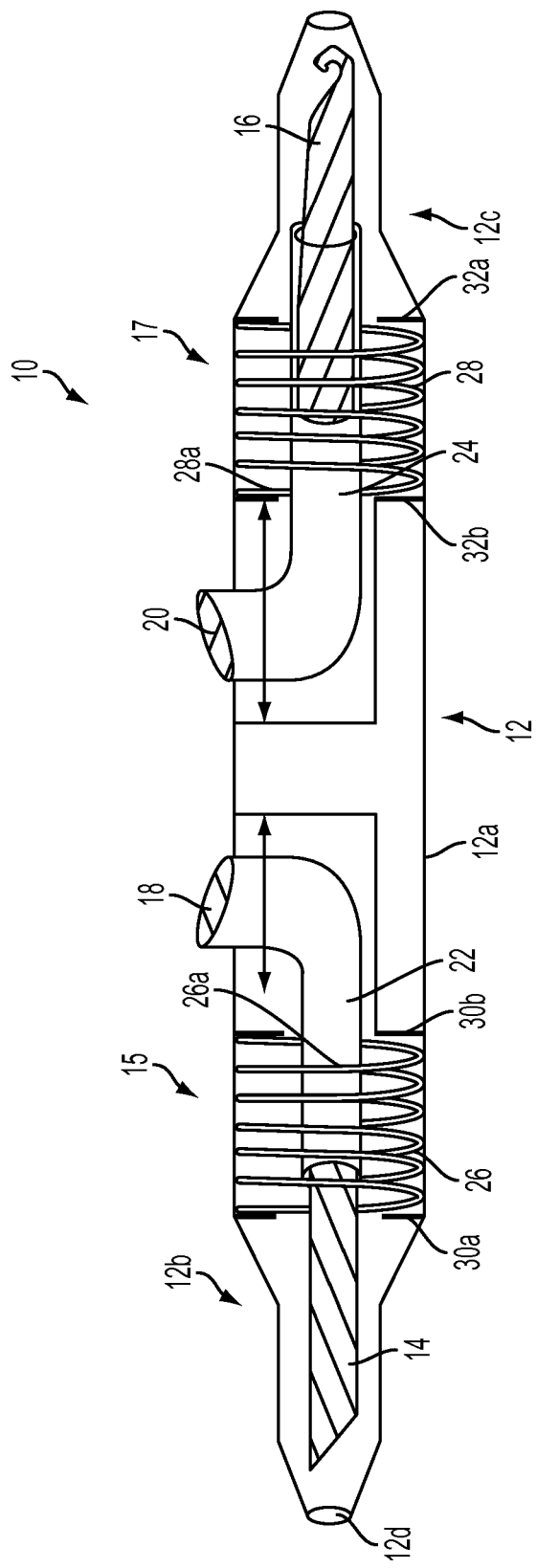
FIG. 1 is a plan view and partial sectional view of a varicose vein removal device in accordance with the present invention, shown with the blade and hook in their retracted or concealed states.
Figure 2:
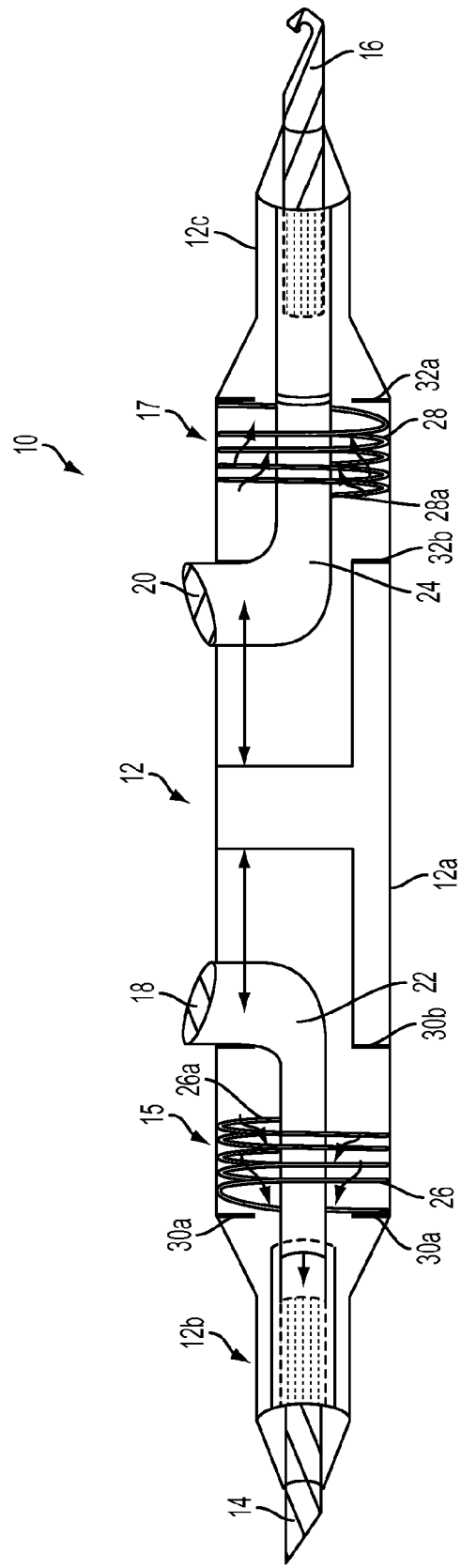
FIG. 2 is a plan view and partial sectional view of the varicose vein removal device of FIG. 1, shown with the blade and hook in their extended or exposed states.

Referring now to the drawings and the illustrative embodiments depicted therein, a phlebectomy device or vein removal device or tool 10 is provided that includes a housing 12 with an extendable/retractable or exposable/concealable blade or scalpel 14 and an extendable/retractable or exposable/concealable hook or retracting element 16 (FIGS. 1 and 2). The vein removal device 10 comprises a self-contained hand held device with both the blade 14 and hook 16 integrated into a hand held housing or module 12 (such as a plastic molded housing or module, such as a plastic housing or module formed by injection molding or the like) to ease the use of the device and to enhance the physician's ability to conduct the two-step process of making an incision in a patient and hooking and retracting a vein, such as a varicose vein, at the incision, as discussed below. As shown in FIGS. 1 and 2, the blade 14 and hook 16 are selectively extended or exposed for use and retracted or concealed for safety when not in use, as also discussed below.

In the illustrated embodiment, housing 12 of vein removal device 10 comprises an elongated housing (such as, for example, an elongated cylindrical-shaped housing or the like) with a central gripping or grasping portion 12a and narrowed end regions 12b, 12c at opposite ends of the central portion 12a. When in its non-use or retracted state (such as shown in FIG. 1), the blade element 14 is disposed within and concealed or housed within blade end region 12b so that no portion of the blade is exposed at the end of the housing 12. Likewise, when in its non-use or retracted state (FIG. 1), the hook element 16 is disposed within and concealed or housed within hook end region 12c so that no portion of the hook is exposed at the end of the housing 12. Optionally, and desirably, blade end region or portion 12b may comprise a transparent or at least partially transparent material or plastic, so that the user of the device 10 may see the blade element or at least the tip or cutting edge of the blade element 14 before it is extended from end portion 12b for making an incision in the patient, in order to assist the physician or operator or user in aligning or positioning the blade at the appropriate location at the patient for the desired incision, as discussed below. Optionally, the hook end portion 12c may also comprise a transparent or at least partially transparent material or plastic, so that the user of the device 10 may see the hook element 16 before it is extended from end portion 12c for hooking a vein at the incision in the patient, as also discussed below.

As can be seen with reference to FIGS. 1 and 2, blade element 14 may be moved between its retracted state (FIG. 1) and its extended or use state (FIG. 2) via a user actuatable input device 18 (such as a button or lever or switch or the like). Likewise, hook element 16 may be moved from its non-use or retracted state (FIG. 1) to its use or extended state or position (FIG. 2) via another user actuatable input 20 (such as a button or lever or switch or the like). The blade 14 and hook 16 may be extended/retracted via a respective extension/retraction mechanism 15, 17, which functions to extend and retract blade 14 and hook 16 responsive to user actuation of the respective user input 18, 20, as discussed below.

Optionally, the input 18 and/or 20 may be selectively and adjustably operated or actuated or moved by the user to control the degree of extension and retraction of the blade 14 and/or hook 16, respectively. For example, the inputs 18 and/or 20 may be ratcheted as they are moved outwardly to extend the blade or hook a desired amount from the end portions 12b and/or 12c for use while the ratcheting mechanism enhances control of the extension of the blade and/or hook, and limits or substantially precludes unintentional retraction of the blade and/or hook during use of the tool or device 10. When retraction of the blade or hook is desired, the respective user input 18, 20 may be depressed or pulled or otherwise adjusted to release the ratcheting mechanism to allow for retraction of the blade or hook.

In the illustrated embodiment, blade extension/retraction mechanism 15 includes a blade attaching or receiving element 22, which receives and/or attaches to blade 14 and is movable to extend/retract blade 14 relative to housing 12, such as in response to movement or actuation of user input 18 (such as movement of a lever or slide element along a slot formed or established partially along handle portion 12a of housing 12). Likewise, hook extension/retraction mechanism 17 includes a hook attaching or receiving element 24, which receives and/or attaches to hook 16 and is movable to extend/retract hook 16, such as in response to movement or actuation of user input 20 (such as movement of a lever or slide element along a slot formed or established partially along handle portion 12a of housing 12).

Optionally, the user inputs 18, 20 and extension/retraction mechanisms 15, 17 may comprise or may be associated with a spring-loaded mechanism, whereby a biasing element or spring 26, 28 is disposed in housing 12 and at or toward the respective end portion 12b, 12c. In the illustrated embodiment, the spring 26 is disposed between opposite walls or flanges or spring stops 30a, 30b at blade end portion 12b, with one end 26a of spring element 26 being attached to or movable with a portion of the blade attaching element 22 and movable user input or lever or slide element 18. Likewise, spring element 28 is disposed between opposite walls or flanges or spring stops 32a, 32b at hook end portion 12c, with one end 28a of spring element 28 being attached to or movable with a portion of the hook attaching element 24 and movable user input or lever or slide element 20.

Thus, movement of user input 18 or 20 to extend blade 14 or hook 16 compresses spring element 26 or 28 against wall or flange 30a or 32a, with spring element 26 or 28 being biased towards its extended or non-compressed state. When the spring is compressed, it imparts a force at the respective attaching element that is towards the retracted state of the blade or hook. The spring elements 26, 28 thus function to retract or urge the blade or hook inwardly responsive to actuation of the user input 18, 20 (to compress or load the spring) and then release (or other actuation) of the user input 18, 20, whereby the spring extends to move or retract the blade or hook.

For example, in response to the user depressing or actuating blade input or button 18, the blade 14 may be extended from blade end portion 12b to make the incision in the patient and, upon release of the input or button 18 (or in response to a secondary actuation of the user input or button), spring 26 may function to quickly urge or move or retract blade element 14 back into end portion 12b. Optionally, the actuating mechanism may automatically retract the blade element immediately after extension thereof, so that the actuating mechanism functions to quickly retract the blade after making the incision so that the blade is extended to make the incision in the patient and immediately retracted so as to be within the blade end portion 12b of housing 12 after the incision has been made. For example, upon the blade reaching a desired or appropriate or preset or selected degree of extension (or in response to the user releasing the lever or button or input 18), spring 26 may function to automatically retract blade 14 as end 26a of spring 26 moves back towards flange 30b. Thus, when the blade is not being used to make an incision in a patient, the blade is retracted in the housing so that the blade is safely concealed within the housing except when in use. Optionally, the blade 14 may be extended via a first actuation of the user input 18 and then retracted (via spring 26) in response to a second actuation of the user input 18 (such as a pressing of the user input to release a locking element or the like that may hold the blade in its extended position).

The actuating mechanism or means for extending the hook element 16 from hook end portion 12c may or may not be include an automatic retraction option, since it is desired that the hook element remain extended for a period of time for a user or physician or operator to hook the vein and retract or extract the vein from the patient through the incision. However, the spring 28 may function to retract the hook 16 in response to a further or secondary or other actuation of the user input 20. For example, a user may press or actuate user input 20 a first time to extend the hook element from end portion 12c and, after removal of the vein or veins from the patient, the user may press or actuate user input 20 a second time to cause automatic retraction of the hook 16 via the biasing function of spring element 28 (such as, for example, in a similar manner as a ball point pen extension/retraction mechanism extends/retracts the pen tip relative to the pen housing).

Optionally, the blade extension/retraction mechanism may comprise a biasing element that urges or imparts extension of the blade element and a biasing element (such as biasing element 26 in FIGS. 1 and 2) that urges or imparts retraction of the blade element. For example, an extending biasing element may function to quickly extend the blade a desired or preset or selected amount from the end portion 12b in response to a user actuating or pressing or moving the user input 18, so as to automatically extend the blade portion to quickly extend and pierce the blade element towards and into the patient at the targeted area. The second or retracting biasing element or spring may function to quickly and automatically retract the blade element back into the end portion 12b after the blade has been extended. In such an embodiment, it is desirable that the blade end portion 12b of housing 12 comprises a transparent material, so that the user may see the blade 14 within the housing end portion 12b and may align the blade (housed within the end portion 12b and with the tip of the blade at or near the opening at the end of the end portion 12b) with the desired incision point. When the retracted blade is aligned with the incision point at the patient (with the blade 14 housed within the end portion 12b and with the tip of the blade at or near the opening 12d at the end of the end portion 12b), the user or physician or operator may depress or actuate the user input button 18 and the device 10 may extend the blade to make the incision (while compressing the spring or biasing element 26 between inner walls 30a, 30b), whereby the spring 26 may automatically retract the blade back to its retracted position. Thus, the incision may be quickly made with minimum exposure of the blade element during the vein removal process. The actuating mechanism or means for extending the hook element 16 from hook end portion 12c would not include such an automatic retraction option, since it is desired that the hook element remain extended for a period of time for a user or physician or operator to hook the vein and retract or extract the vein from the patient through the incision.

Thus, the varicose vein removal device or tool 10 provides a unitary or integrated device or module that includes and houses both the blade element and a hook element so that a user or physician or operator using the tool need not have to deal with two separate devices to perform and complete the vein removal process. The vein removal device is easily operated by a user to selectively extend the blade element for making an incision in a patient (whereby the blade element may be manually or automatically retracted back to its retracted state upon completion of its incision). The blade removal tool also provides for selective extension of the hook element, whereby when the hook is extended, the user or physician may insert the hook end into the patient through the incision and may hook the vein that is to be removed, whereby the physician may retract and extract the vein in a known manner. The vein removal device or tool of the present invention may comprise a disposable device or tool, whereby a user or physician may use the tool for a single patient or operation or procedure, and may dispose of the tool or device upon completion of the procedure. Optionally, and desirably, the housing and/or actuating mechanisms and/or user inputs may comprise a plastic or polymeric material, such that the tool components may be molded or injection molded out of the plastic or polymeric material to reduce costs of the disposable tool. The user input mechanism or extension/retraction mechanisms or means may comprise a plastic or polymer blade/hook receiving or attaching portion that receives or attaches to a stainless steel blade and stainless steel hook, since it is desirable that these elements comprise stainless steel (or other surgical grade materials, such as titanium or the like).

Figure 3:
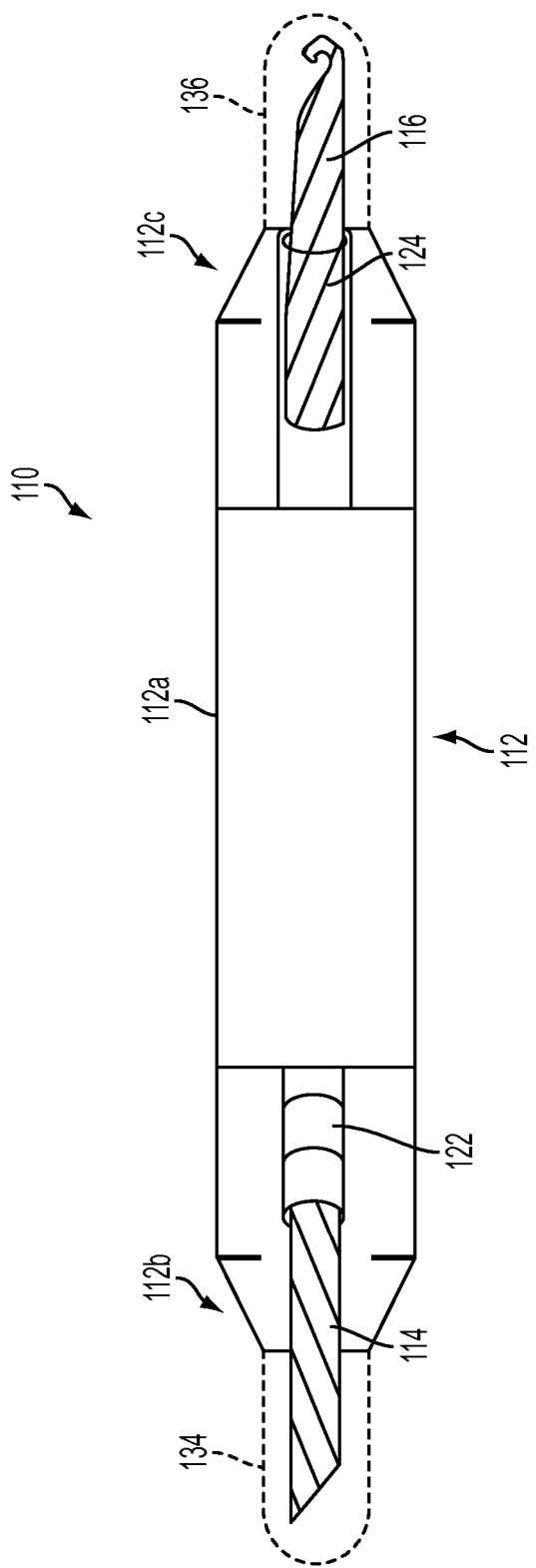
FIG. 3 is a plan view and partial sectional view of another varicose vein removal device in accordance with the present invention.

Although shown in FIGS. 1 and 2 as having the blade and hook selectively extendable and retractable relative to respective end portions of the housing, it is envisioned that a vein removal tool of the present invention may otherwise provide for selective exposure of the blade element and/or hook element, while remaining in the spirit and scope of the present invention. For example, and with reference to FIG. 3, a phlebectomy device or varicose vein removal device or tool 110 comprises a housing 112 having a central gripping or grasping portion 112a and opposite end portions 112b, 112c for receiving and at least partially housing a blade element 114 and hook element 116, respectively. As shown in FIG. 3, blade element 114 is partially received within end portion 112b, and is held there at the blade receiving or attaching element 122 within housing 112, such that the cutting edge or tip or portion of blade 114 protrudes from end portion 112b. Similarly, hook element 114 is attached to or retained by a hook retaining or receiving or attaching element 124 within in housing end portion 112c, such that the end or hook portion of hook element 116 extends from and is exposed at end portion 112c of housing 112 of vein removal device 110. A cover element 134 may be removably attached at end portion 112b for selectively covering and exposing the cutting edge of blade element 114, while a cover element or cap 136 may be removably attached at end portion 112c of housing 112 for selectively exposing and cover or concealing hook element 116 at end portion 112c of housing 112 of vein removal tool 110. Thus, when a user or physician or operator is to use the vein removal tool 110, the user may first remove cover 134 from blade end 112b to expose the cutting edge of the blade element 114 for making an incision in the patient. After the incision is completed, the user may replace the cover element or cap 134 at end portion 112b to cover the blade element 114, and may remove the cover of cap 136 from end portion 112c to expose the hook element 116. The user may reverse the tool and then may use the exposed hook portion to insert the hook into the incision end and hook and remove the vein from the patient.

Although shown and described above as having a blade element selectively protruding from or selectively being exposed at one end of the device and a hook element selectively protruding from or selectively being exposed at the other end of the device, it is envisioned that a varicose vein removal device or tool of the present invention may have the blade element and hook element selectively protruding from the same end or region or portion of the device. For example, and with reference to FIG. 4, a varicose vein removal device or tool 210 may comprises a housing 212 having a gasping portion 212a and an end portion 212b that receives and retains a blade element 214 and a hook element 216 therein. Each of the blade element and hook element are selectively movable at end portion 212b to selectively extend either the blade element 214 or the hook element 216 at the end of the vein removal device 210. As can be seen with reference to FIG. 4, the blade element 214 may be selectively moved or protruded or extended via actuation of a user input button or switch or lever or slide 218 to move the end or cutting edge or tip of the blade element outward from the end portion 212b from making an incision in the patient. Likewise, the hook element 216 may be selectively protruded or extended via actuation of the user input or button or switch or lever or slide 220 to move the hook outward from the end portion 212b for hooking a vein and extracting the hooked vein from the patient.

Figure 4:
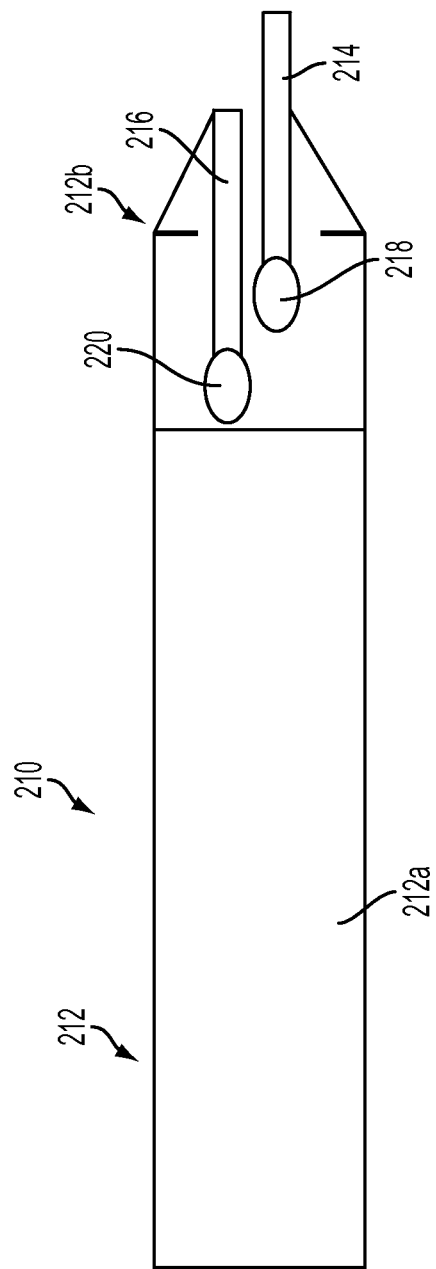
FIG. 4 is a plan view and partial sectional view of another varicose vein removal device in accordance with the present invention.

The user inputs or switches or buttons may be selectively actuated by the user to independently extend either the blade or the hook from the end of the tool. For example, the user may first extend the blade (as shown in FIG. 4) to expose the tip or cutting edge of the blade when making an incision or incisions, and then may retract the blade when the incision is completed (and optionally the retraction and extension may be spring loaded and/or automatic, such as described above). After the blade has been retracted into the end portion 212b, the user may actuate or remove or adjust the user input 220 to extend the hook element from the end portion 212b for hooking and extracting the vein from the patient. Further, other means for selectively extending and retracting and/or exposing and covering the blade element and hook element at either or both ends of a vein removal tool may be implemented, while remaining within in the spirit and scope of the present invention.

Optionally, the hook element or elements 16, 116, 216 of the vein removal tools or devices of the present invention may comprise any suitable hook shape or form for inserting into an incision made in the patient and hooking under and partially around a targeted vein for pulling and extracting a vein from the patient, while limiting slippage of the vein off of the hook during the removal/extraction process. For example, and as shown in FIG. 5, the hook portion 40 of the hook element 14 may comprise a J-shaped hook portion, such as similar to know hook-shaped tools currently used in vein extraction procedures.

Figure 5:
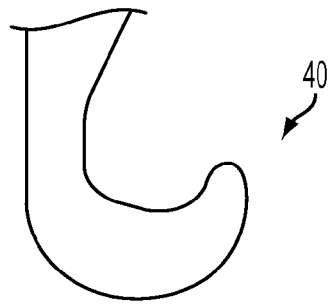
FIG. 5 is an enlarged plan view of a hook or removal element suitable for use with the varicose vein removal device of the present invention.
Figure 6:
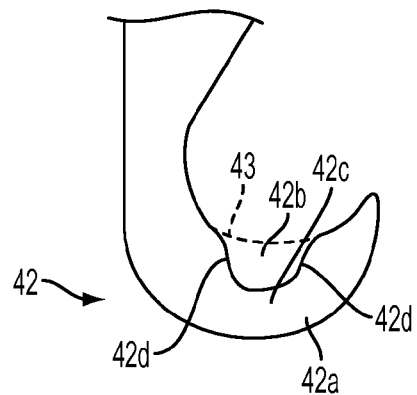
FIGS. 6-9 are enlarged plan views of other hooks or removal elements of the present invention.

Optionally, and with reference to FIG. 6, a hook 42 of a hook element for use with a phlebectomy tool or device may comprise a generally J-shaped hook portion 42a, with a recess or indentation 42b along the lower portion 42c of the J-shaped hook portion 42a (with the phantom line 43 in FIG. 6 showing the inner surface of a typical phlebectomy hook or tool, such as a typical J-shaped hook 40 as shown in FIG. 5). The indentation or recess 42b is sized to receive the vein therein and has steeper side walls 42d than the typical J-shaped hook to limit or substantially preclude unintentional slippage or loss of the vein at the hook during the extraction process.

Figure 7:
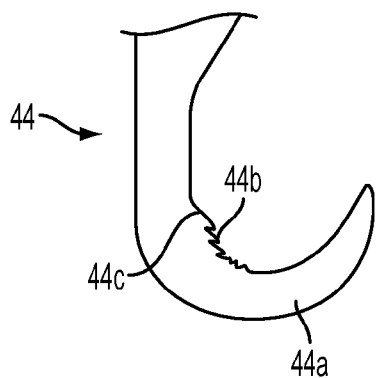
Figure 8:
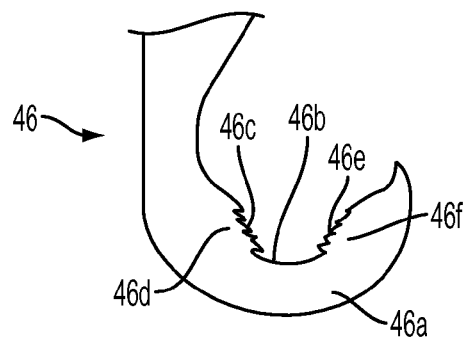

Optionally, and with reference to FIG. 7, a hook 44 of a hook element for use with a phlebectomy tool or device may comprise a generally J-shaped hook portion 44a, with a plurality of spikes or teeth or protrusions 44b extending generally radially from the inner surface 44c of the hook portion 44a, such as along the posterior up-slope of the inner angulated portion of the hook portion. Thus, the hook portion 44a provides an abrasive surface at a portion of the inner surface of the hook portion, with the abrasive surface being composed of multiple small pointed extensions protruding from the surface (such as approximately $\frac{1}{1000}$ of a mm from the surface) to engage and grip a vein at the hook to limit or substantially preclude movement of the vein along the hook during the extraction process. Optionally, the inner surface 44c of the hook portion 44a may comprise a generally circular curvature or generally constant of radius of curvature, or the inner surface may include a recess or depression formed therein (such as shown in FIG. 6), with the teeth or abrasive surface established along one or both of the steeper slope side walls of the recess or depression. For example, and as shown in FIG. 8, a hook 46 of a hook element for use with a phlebectomy tool or device may comprise a generally J-shaped hook portion 46a with a recess or depression 46b formed at its inner surface, and with a plurality of teeth or abrasive elements or protrusions 46c disposed along one of the steeper side walls 46d of the recess or depression 46b, and a plurality of teeth or abrasive elements or protrusions 46e formed or established at and along the opposite steeper side wall 46f of the recess or depression 46b. The hook portion 46a thus includes a plurality of protruding spikes or teeth 46c, 46e located at both the interior and posterior slopes or slides of the recess or depression (and the spikes may extend in a suitable length or distance, such as, for example, approximately $\frac{1}{1000}$ mm or thereabouts). Optionally, and with reference to FIG. 9, a hook 48 may comprise a generally J-shaped hook portion 48a with an inner surface 48b that has a plurality of extensions or spikes or teeth or protrusions 48c located along the entirety of the inner surface or portion 48b of the curved tip of the hook portion 48a.

Figure 9:
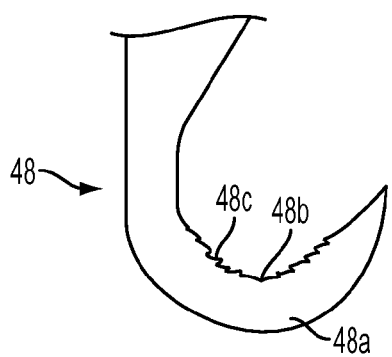

Thus, the present invention provides for a curved hook that is configured or formed or shaped to provide enhanced gripping and stabilization of a vein that is captured at the hook to limit or substantially preclude movement or slippage of the vein relative to the hook during the extraction process. The additional deeper curve or recess in the J-shaped hook (such as shown in FIGS. 6 and 8) functions to assist in stabilizing the captured vein, while the addition of the jagged surfaces or serrated surfaces or abrasive surfaces (such as shown in FIGS. 7-9) assist in gripping the captured vein to limit movement of the vein relative to the hook during the vein extraction process. The hooks and hook configurations of the present invention thus provide for enhancing the ability for the hook to capture the target vein (the vein being removed) and the hooks function to limit or substantially preclude sliding of the vein off the hook via the stabilization means and the surface spikes or teeth that may penetrate the vein wall to retain the vein in place relative to the hook throughout the vein extraction procedure.

The hooks of the present invention thus provide various capturing features and/or retaining features, which all limit or substantially prevent the sliding out of the vein from the hook. The additional curve or recess at the inner surface of the hook functions to store and stabilize the newly captured vein to assist in limiting slippage of the vein relative to the hook. The additional recess or pouch provides a deeper and steeper downward and upward slope of the inner surface of the angled portion of the tip of the hook and may be created by a drop or recess in the inner surface of the hook, such as a recess that creates a semi-circle shape with steep slopes on each side of the center of the recess that act as walls that would limit or substantially preclude a vein from slipping out of the hook during the extraction process. The optional addition of the spikes or serrations or protrusions further enhances the hook to limit slippage of a vein relative to the hook during the vein extraction procedure. The spikes or serrations may comprise any suitable form, and may have sharp tips that protrude at an angle relative to the surface of the hook (such as an angle of, for example, approximately 35 degrees or thereabouts relative to the downward and upward slope of the inner surface of the hook). The particular angle or angles of the spikes or protrusions may vary depending on the particular application of the vein removal tool or device.

Thus, the present invention provides a varicose vein removal tool or device or phlebectomy tool or device designed for removal of unwanted veins from a patient. The tool or device of the present invention combines a blade or other sharp object or cutting means (for penetrating the skin of the patient at the site of entry for the phlebectomy hook) and a hook or hook element for extracting the targeted vein through the incision or piercing of the patient, all in a single hand-held device or tool. Optionally, and desirably, the removal tool may be disposed after use. The device thus may be sterilized and packaged as a single unit, and used by a user or physician and then disposed of, thereby substantially easing the process to the physician and physician's office.

The blade of the device of the present invention is initially housed or concealed in the device housing when in its non-use state. When activated and pushed forward or extended or exposed, such as via actuation of a button or other user input at the outer surface of the device, the blade becomes active and extends from the device and penetrates the target area of the patient. Optionally, and desirably, the tool includes a safety feature to automatically and quickly retract the blade back into the housing after use of the blade, thereby enhancing the safety features of the device for the safety of both the patient and user or physician. The retraction mechanism may be based on a spring system that stores the energy for the retraction during the advancement of the blade by the operator (such as via compression of a spring as the blade is advanced, whereby, upon release, the spring, which is biased towards its extended position, extends to retract the blade). Thus, as the operator presses or moves the user input or button to extend the blade, the movement of the button compresses the spring or biasing element, and, upon release of the button by the operator (or upon the blade reaching a preset or preselected degree of extension or advancement), the spring quickly urges that blade back towards and to its initial retracted position.

Optionally, and desirably, the end portion of the device that houses the blade is transparent or clear or substantially transparent or substantially clear for the operator to visualize the sharp end of the blade at all times during the procedure, including before the blade is extended and as the blade is moved near to and into alignment with the targeted area of the patient. The transparent or clear portion provides an additional safety feature and allows for constant vision and viewability of the tip of the blade and thus monitoring of the motion of the blade during alignment of the blade with the target area of the patient and during the incision making process or procedure.

Optionally, and desirably, the extension mechanism may cause extension of the blade at a rapid speed or rate to quickly penetrate the target area and thus reduce the discomfort to the patient. The mechanism also quickly retracts the blade back into the device at a rapid rate to enhance safety of the device to both the patient and the operator. Optionally, the blade may be advanced to a preset distance depending on the application. The operator may preset the distance or degree of extension to provide an appropriate cutting depth so that, when actuated, the blade extends the appropriate or pre-selected amount to penetrate the patient the desired amount (and optionally rapidly extending the desired or pre-selected amount and then retracting back into the housing after the incision is made). For example, the operator may select an extension of about two mm and then may actuate the actuator or user input to cause the blade to rapidly extend about two mm and rapidly retract back into the housing, thereby quickly making a small incision in the patient at the targeted area.

Optionally, the blade extension/retraction mechanism may provide an operator with various options, including the ability of advancing the blade a desired amount or pre-selected amount and stabilizing or holding the blade in place at its extended state, or placing the device at the target area of the patient and causing the blade to rapidly extend to the extended or exposed or cutting orientation, with no automatic retraction of the blade, or placing the device at the target area of the patient and extending the blade to make the incision and rapidly retracting the blade automatically after the incision has been made (this third option provides the greatest safety for the patient and the operator as the blade is exposed only during the incision procedure and is concealed within the housing of the device at all other times). The motion of the blade may be achieved via a spring-loaded system having a spring located between opposite spring stops or walls within the housing. The spring stops or walls allow the spring to be compressed to store the energy needed to provide the rapid speed and force on extension that is required or desired to penetrate the target area of the patient. The spring-loaded mechanism may be activated by the button or user input located at the housing of the device and at or near the end of the device that houses the blade. For example, the user input or pusher or button may be housed in a space of the body of the device and may have a surface button or region that allows the operator to actuate the mechanism to perform any of the various extension/retraction methods described above.

The user input or button or pusher is connected to the base of the blade within the body of the device and may have a 1:1 reactivity between the blade and the pusher, which provides the operator enhanced precision of the motion of the blade as the blade moves with the finger or thumb actuated user input or pusher at the housing, thereby increasing the success rate and safety of the device. Optionally, the extension/retraction mechanism may include a locking mechanism that may lock the blade in any position the operator desires, such as via a ratcheting mechanism or the like.

The above descriptions are those of current embodiments of the invention. Various alterations and changes can be made without departing from the spirit and broader aspects of the present invention, which is intended to be limited only by the scope of the appended claims, which are to be interpreted in accordance with the principles of patent law including the doctrine of equivalents.

The invention claimed is:

1. A vein removal device, comprising:
a housing longitudinally extending from a first end portion to a second end portion;
a blade element, including a cutting edge, disposed at least partially within the first end portion of the housing;
a hook element disposed at the second end portion of the housing; and
a first user input device, operably coupled to the blade element, actuatable from and between a resting position and a depressed position along angular direction relative to the extension of the housing,
wherein actuation of the first user input device from the resting position toward the depressed position causes the blade element to move relative to the housing from a retracted position within the first end portion to an extension position in which the cutting edge is selectively exposed a distance that is proportionate to an amount of actuation of the first user input device.

2. The vein removal device of claim 1, further comprising a second user input device, operably coupled to the hook element, actuatable from and between a resting position and a depressed position along angular direction relative to the extension of the housing,
wherein actuation of the second user input device from the resting position toward the depressed position causes the hook element to move relative to the housing from a retracted position within the second end portion to an extension position in which the hook element is selectively exposed a distance that is proportionate to an amount of actuation of the second user input device.

3. The vein removal device of claim 1, wherein the hook element is generally fixed relative to the housing and is selectively exposed via removal of at least one cover element at the second end portion of the housing.

4. The vein removal device of claim 1, wherein the blade element is biased toward the extension position via a biasing element, and wherein the biasing element urges the blade element toward the extension position responsive to actuation of the first user input device.

5. The vein removal device of claim 4, wherein the blade element is extended to the extension position and then automatically retracted from the extension position in response to actuation of the first user input device.

6. The vein removal device of claim 1, wherein the blade element is biased towards the retracted position via a biasing element.

7. The vein removal device of claim 6, wherein the biasing element urges the blade element toward the retracted position responsive to a further actuation of the first user input device.

8. The vein removal device of claim 1, wherein a stationary portion of the first end portion of the housing is substantially transparent so that the blade element is viewable by a user before the blade element is moved to the extension position.

9. The vein removal device of claim 1, wherein the hook element is selectively exposed for hooking a vein at an incision in a patient and retracting the vein.

10. The vein removal device of claim 1, wherein the housing comprises a polymeric housing.

11. The vein removal device of claim 1, wherein the vein removal device comprises a disposable single-use vein removal device.

12. The vein removal device of claim 1, wherein the hook element comprises a generally J-shaped hook portion.

13. The vein removal device of claim 12, wherein the generally J-shaped hook portion has a narrowed recess along an inner curved portion for receiving a portion of a vein therein.

14. The vein removal device of claim 12, wherein the generally J-shaped hook portion has a plurality of spikes or teeth or protrusions extending generally radially from an inner surface.

15. The vein removal device of claim 1, wherein the first user input device is actuatable along an angular direction that is substantially perpendicular to the extension of the housing.

16. The vein removal device of claim 1, wherein the first user input device is located closer to the first end portion of the housing than the second end portion of the housing.

17. The vein removal device of claim 1, wherein the first user input device is operably coupled with a ratcheting mechanism.

18. The vein removal device of claim 1, wherein a connection between the first user input device and the blade element is configured to provide a 1:1 reactivity between actuation of the first user input device and blade element movement relative to the housing.

19. A vein removal device, comprising:
a housing longitudinally extending from a first end portion to a second end portion;
a blade element, including a cutting edge, disposed at least partially within the first end portion of the housing;
a hook element disposed at the second end portion of the housing;
a first user input device, operably coupled to the blade element and positioned closer to the first end portion of the housing than the second end portion of the housing, actuatable from a resting position toward a depressed position along substantially perpendicular direction relative to the extension of the housing, wherein actuation of the first user input device from the resting position toward the depressed position causes the blade element to move relative to the housing from a retracted portion within the first end portion to an extension position in which the cutting edge is exposed; and
a single biasing element positioned and configured to bias the blade element toward the retracted position.

20. The vein removal device of claim 19, wherein the hook element is generally fixed relative to the housing and is selectively exposed via removal of at least one cover element at the second end portion of the housing.

21. The vein removal device of claim 19, wherein the hook element is selectively exposed via actuation of a second user input device that imparts a movement of the hook element relative to the housing and toward an extension position in which the hook element is exposed.

22. The vein removal device of claim 19, wherein the blade element is extended to the extension position and then automatically retracted from the extended position in response to actuation of the first user input device.

23. The vein removal device of claim 19, wherein the single biasing element biases the blade element toward the retracted position when the first user input device is unactuated.

24. The vein removal device of claim 19, wherein the single biasing element urges the blade element toward the retracted position responsive to a further actuation of the first user input device.

25. The vein removal device of claim 19, wherein a stationary portion of the first end portion of the housing is substantially transparent so the blade element is viewable by a user of the varicose vein removal device before the blade element is moved toward the extension position.

26. The vein removal device of claim 19, wherein the first user input device operates to adjust a degree of extension of the blade element responsive to a user selectively actuating the first user input device.

27. The vein removal device of claim 19, wherein the hook element is selectively exposed for hooking a vein at an incision in a patient and retracting the vein.

28. The vein removal device of claim 19, wherein the hook element comprises a generally J-shaped hook portion having a narrowed recess along an inner curved portion for receiving a portion of a vein therein.

29. The vein removal device of claim 19, wherein the hook element comprises a generally J-shaped hook portion having a plurality of spikes or teeth or protrusions extending generally radially from an inner surface.

30. The vein removal device of claim 19, wherein the hook element comprises a generally J-shaped hook portion, wherein the generally J-shaped hook portion comprises an inner curved portion having a narrowed recess for receiving a portion of a vein therein, and wherein the generally J-shaped hook portion comprises a plurality of spikes or teeth or protrusions extending generally radially from the inner curved portion.

* * * * *